United States Patent
Stem

(10) Patent No.: US 10,213,595 B2
(45) Date of Patent: Feb. 26, 2019

(54) METHODS AND DEVICES FOR IHIBITING TISSUE GROWTH FROM RESTRICTING A STRAIN RELIEF LOOP OF AN IMPLANTABLE MEDICAL LEAD

(71) Applicant: Medtronic, Inc., Minneapolis, MN (US)

(72) Inventor: Bryan D. Stem, Minneapolis, MN (US)

(73) Assignee: MEDTRONIC, INC., Minneapolis, MN (US)

(*) Notice: Subject to any disclaimer, the term of this patent is extended or adjusted under 35 U.S.C. 154(b) by 0 days.

(21) Appl. No.: 15/645,904

(22) Filed: Jul. 10, 2017

(65) Prior Publication Data
US 2017/0304607 A1    Oct. 26, 2017

Related U.S. Application Data

(62) Division of application No. 14/568,690, filed on Dec. 12, 2014, now Pat. No. 9,700,714.

(60) Provisional application No. 61/919,374, filed on Dec. 20, 2013.

(51) Int. Cl.
*A61N 1/05* (2006.01)

(52) U.S. Cl.
CPC .......... *A61N 1/05* (2013.01); *A61B 2562/187* (2013.01)

(58) Field of Classification Search
None
See application file for complete search history.

(56) References Cited

U.S. PATENT DOCUMENTS

| | | | | |
|---|---|---|---|---|
| 4,013,081 A | * | 3/1977 | Kolenik | A61N 1/3752 607/36 |
| 5,861,023 A | * | 1/1999 | Vachon | A61N 1/0563 607/121 |
| 9,034,000 B2 | * | 5/2015 | North | A61N 1/375 606/148 |
| 2011/0060311 A1 | * | 3/2011 | Barolat | A61N 1/375 604/523 |
| 2012/0150202 A1 | * | 6/2012 | Chen | A61B 17/0401 606/148 |

* cited by examiner

*Primary Examiner* — Kennedy Schaetzle
(74) *Attorney, Agent, or Firm* — Withers & Keys, LLC

(57) ABSTRACT

The function of a strain relief loop of an implantable medical lead is preserved by inhibiting restriction of the strain relief loop from tissue growth onto the strain relief loop. The restriction may be inhibited by either obstructing tissue growth and/or by utilizing a mechanical advantage to overcome the restriction. The tissue growth may be obstructed be isolating the interior of the strain relief loop such as by enclosing the strain relief loop or including an object within the loop. The mechanical advantage to overcome restriction from tissue growth may be provided in various ways such as utilizing a spring loaded mechanism or a structure such as an elastic mesh, tube, or mold having an inherent bias toward a steady state position.

16 Claims, 13 Drawing Sheets

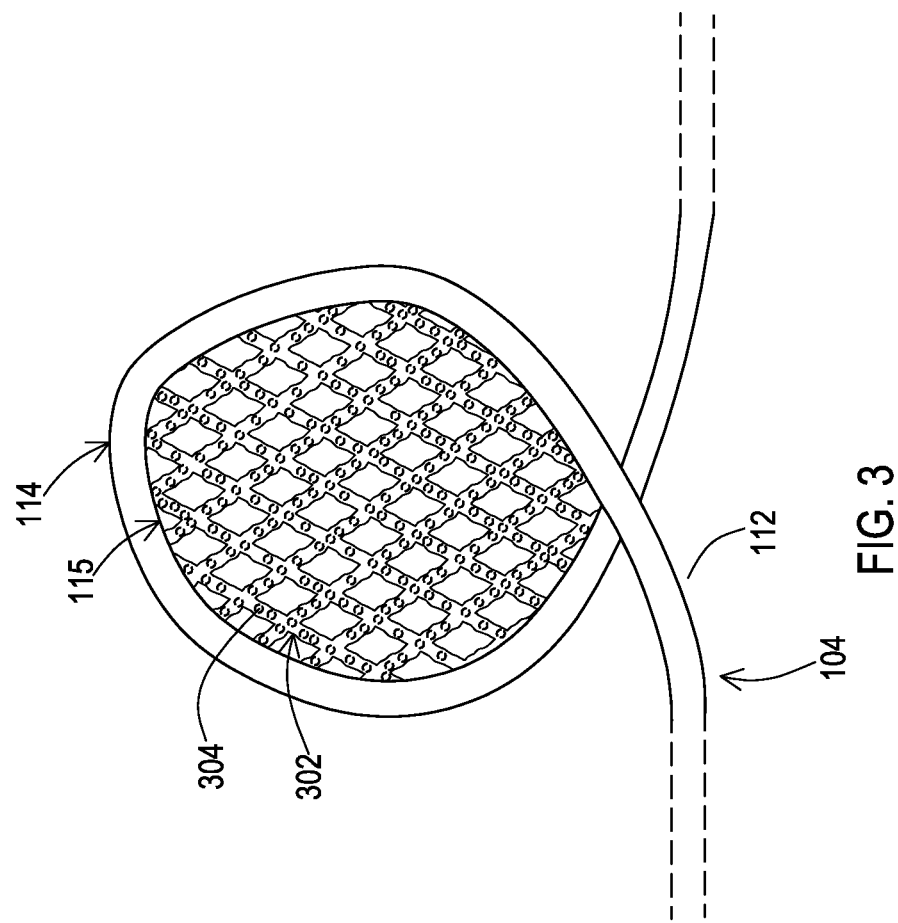

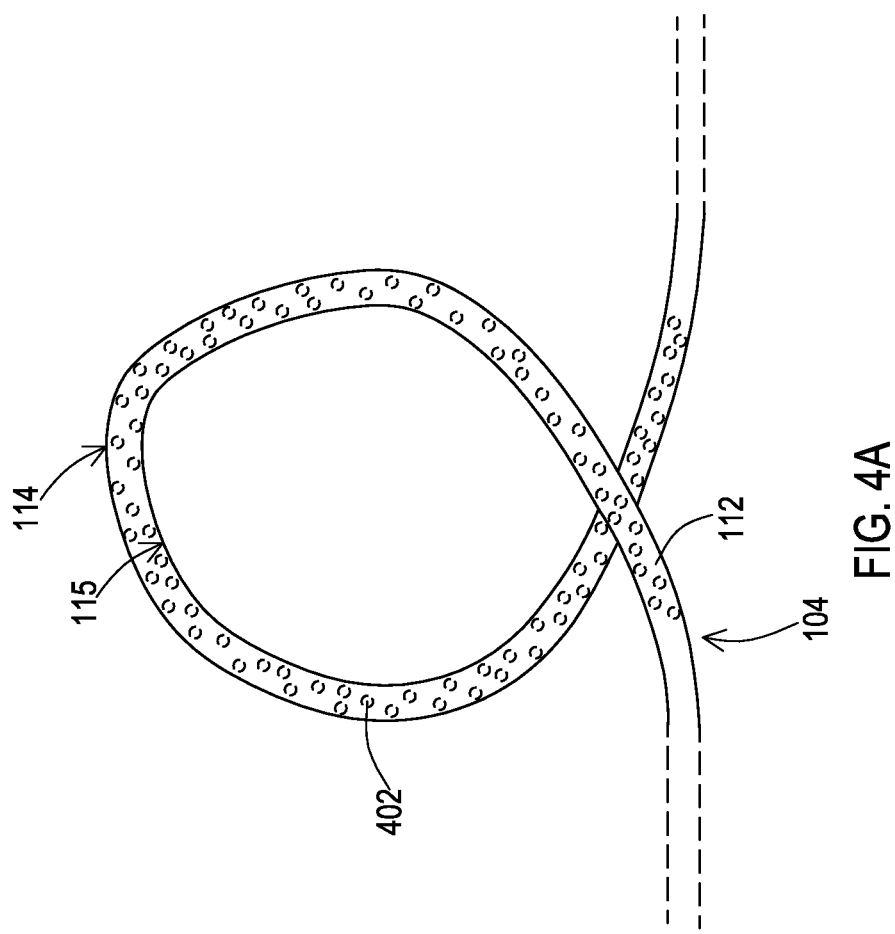

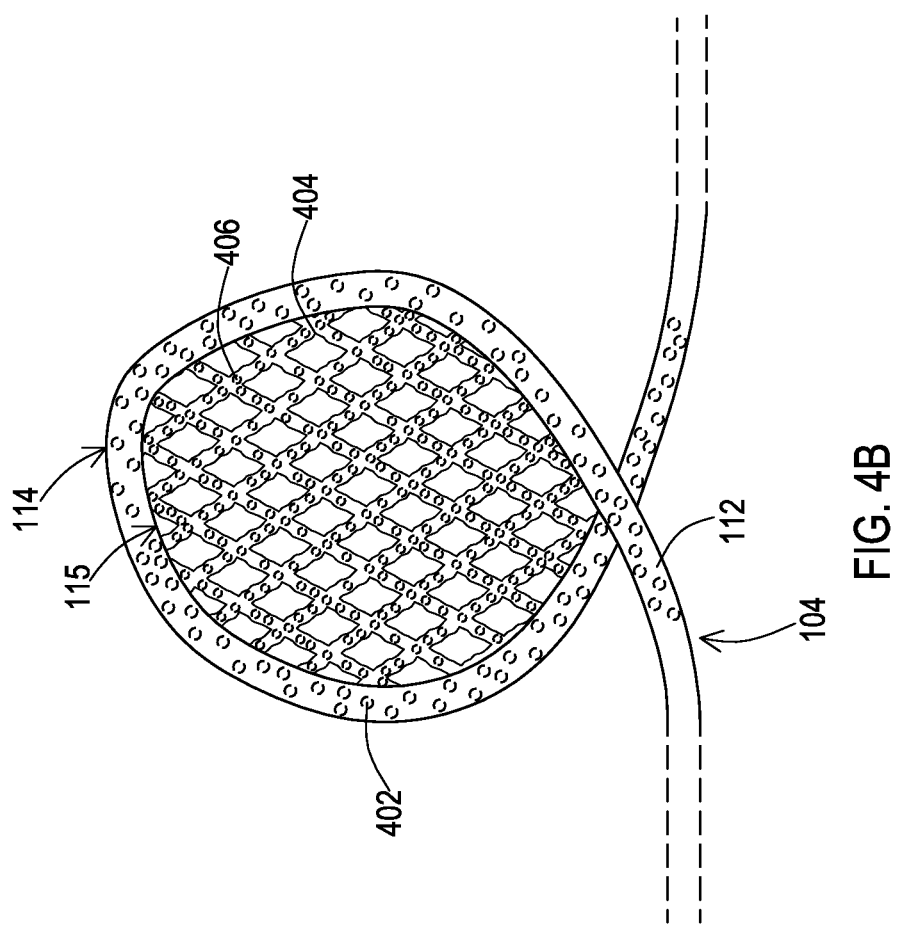

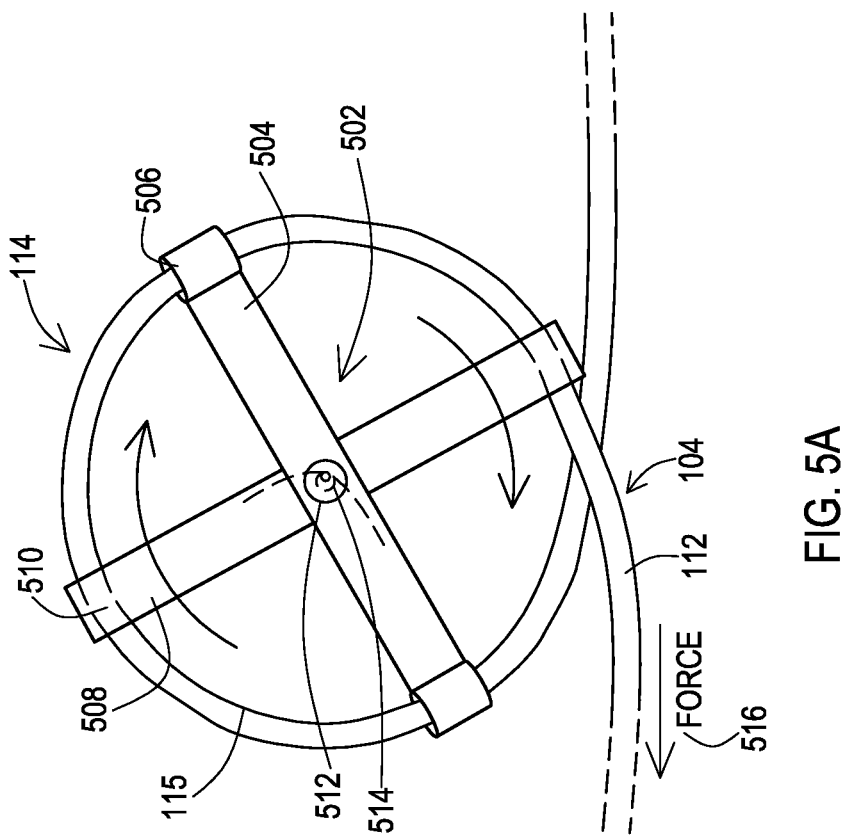

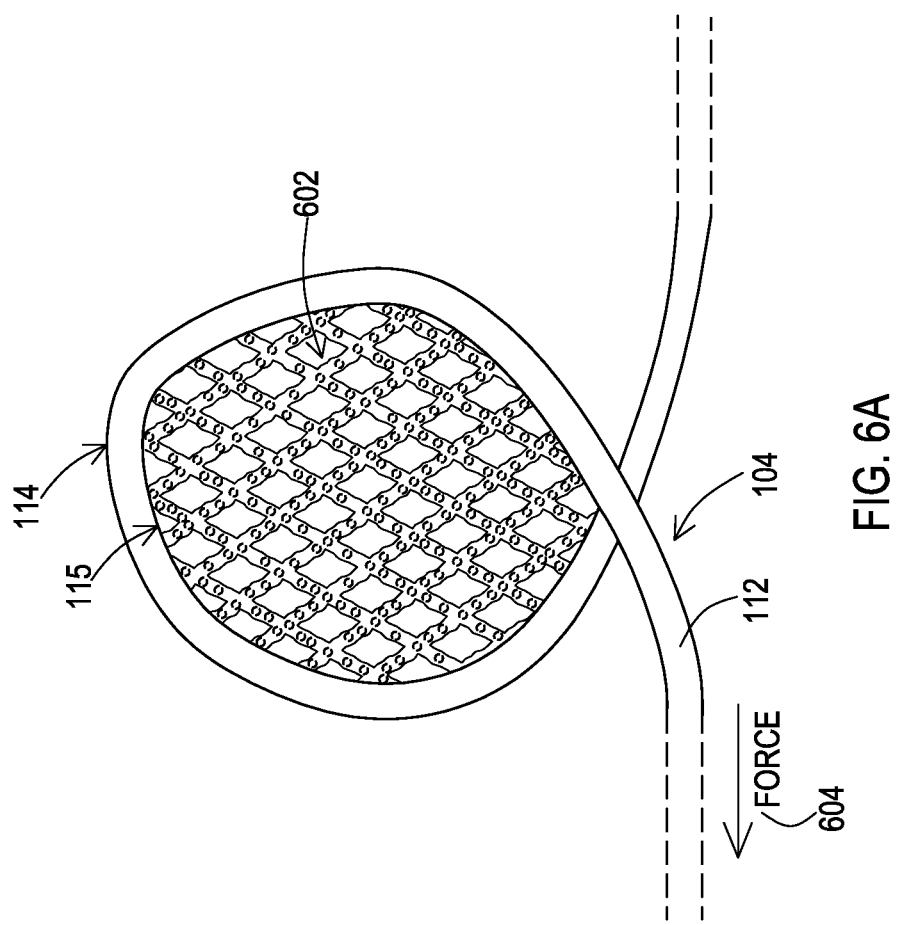

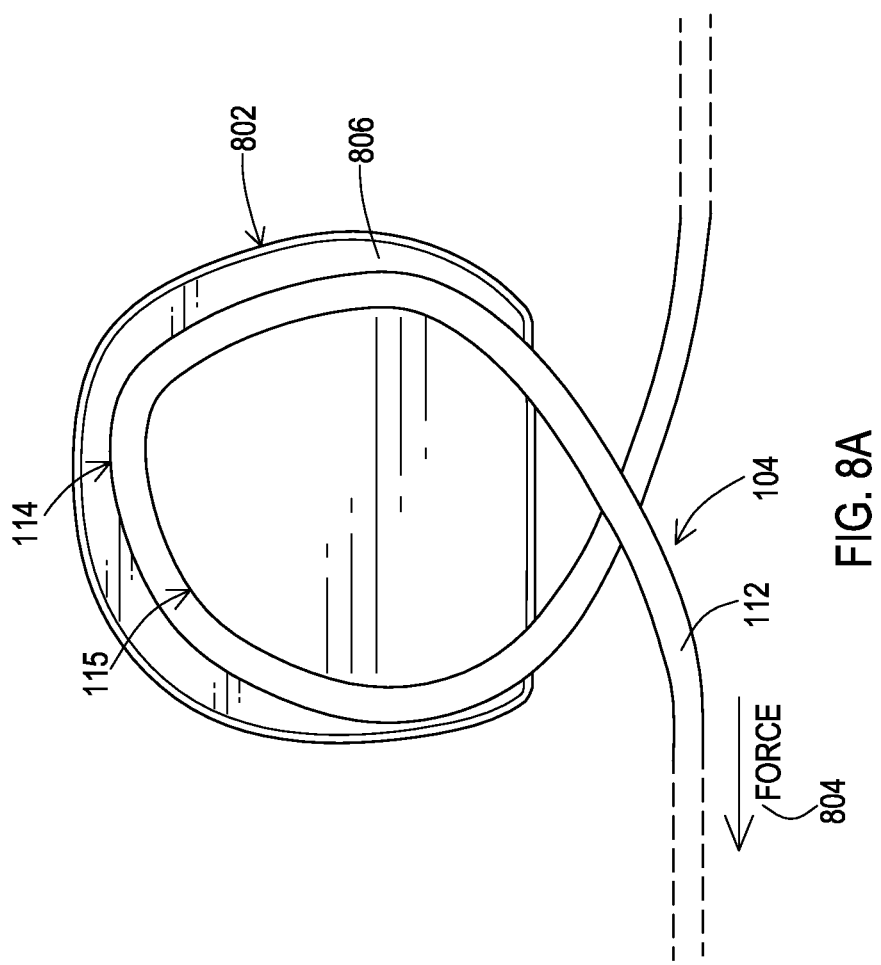

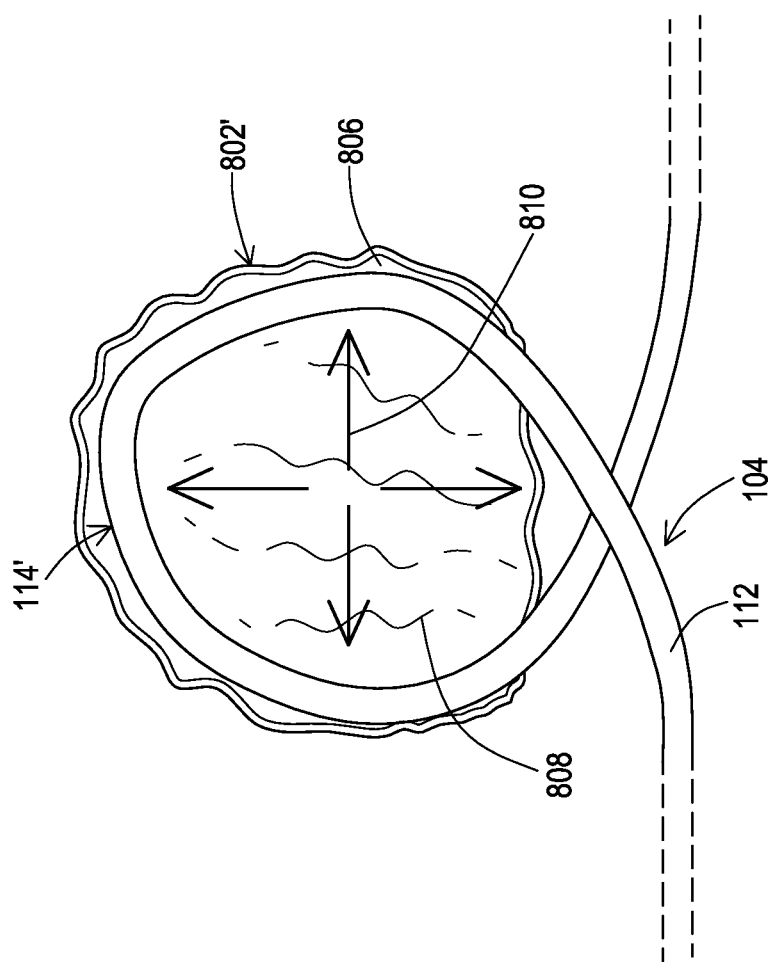

METHODS AND DEVICES FOR IHIBITING TISSUE GROWTH FROM RESTRICTING A STRAIN RELIEF LOOP OF AN IMPLANTABLE MEDICAL LEAD

RELATED APPLICATIONS

The present application is a divisional of U.S. Pat. No. 9,700,714, filed on Dec. 12, 2014, which claims priority to U.S. App. No. 61/919,374, filed on Dec. 20, 2013.

TECHNICAL FIELD

Embodiments relate to strain relief loops of implantable medical leads. More particularly, embodiments relate to inhibiting tissue growth from restricting strain relief loops.

BACKGROUND

Implantable medical systems include implantable stimulators that are positioned at an implantation site and implantable medical leads that extend from the implantation site to a target site within the body of a patient. The implantable medical leads have a proximal end that is coupled to the implantable stimulator and have a distal end that includes electrodes at the target site. The implantable medical leads include conductors within a lead body, and these conductors carry electrical stimulation signals from the electrical stimulator to the electrodes to deliver the electrical stimulation signals to the tissue at the target site.

An issue that occurs for a period of time immediately following implantation of the medical lead involves the distal end of the lead being displaced from the target site due to certain bending movements of the patient prior to the distal end of the lead being adequately encapsulated by tissue growth. To address this displacement issue, during implantation a strain relief loop is created with the lead in order to allow the patient to move while allowing the distal end of the lead to remain positioned at the target site. However, the strain relief loop may experience encapsulation from tissue growth prior to the distal end of the lead being adequately encapsulated by tissue. This encapsulation of the strain relief loop limits the ability of the strain relief loop to function properly to maintain the position of the distal end of the lead.

SUMMARY

Embodiments address issues such as these and others by providing methods and devices that inhibit tissue growth from restricting the function of the strain relief loop of the implantable medical lead. One manner of doing so is to inhibit the tissue growth from encapsulating the strain relief loop. This may be done in various ways, such as by obstructing at least the interior of the loop so that tissue does not fill the interior and adhere to the loop and/or by utilizing a tissue growth inhibitor as a coating or dopant of the lead or the object obstructing the interior of the loop. Another manner of doing so is to establish a mechanical advantage by applying a bias onto the loop which allows the loop to function to provide slack but biases the loop toward a steady state size when the loop size changes from the steady state due to movements by the patient.

Embodiments provide a method of inhibiting tissue growth from restricting a strain relief loop of an implantable medical lead. The method involves positioning a lead body of the implantable medical lead to produce a strain relief loop. The method further involves coupling an object to the lead such that the object obstructs an area defined by an inner circumference of the loop while allowing the strain relief loop to provide strain relief.

Embodiments provide a method of inhibiting tissue growth from restricting a strain relief loop of an implantable medical lead. The method involves providing a lead body of the lead with a tissue growth inhibitor. The method further involves positioning the lead body of the implantable medical lead to produce a strain relief loop such that the tissue growth inhibitor is present at the loop.

Embodiments provide a method of inhibiting tissue growth from restricting a strain relief loop of an implantable medical lead. The method involves providing a lead body that forms a strain relief loop. The method further involves providing an object that is coupled to the strain relief loop, that has a steady state position providing a first diameter of the strain relief loop, and that applies a bias toward the steady state position when force applied to the implantable lead causes the strain relief loop to have a second diameter that differs from the first diameter.

Embodiments provide an apparatus that inhibits tissue growth from restricting a strain relief loop. The apparatus includes an implantable lead forming the strain relief loop and an object that is coupled to the strain relief loop. The object has a steady state position providing a first diameter of the strain relief loop, and the object applies a bias toward the steady state position when force applied to the implantable lead causes the strain relief loop to have a second diameter that differs from the first diameter.

DESCRIPTION OF THE DRAWINGS

FIG. 3 shows the strain relief loop portion of the lead with a second embodiment of a strain relief holder that inhibits restriction by tissue growth.

FIGS. 4A and 4B show embodiments of the strain relief loop portion of the lead that inhibits restriction by tissue growth.

FIGS. 5A and 5B show two states of the strain relief loop portion of the lead with a third embodiment of a strain relief holder that inhibits restriction by tissue growth.

FIGS. 6A and 6B show two states of the strain relief loop portion of the lead with a fourth embodiment of a strain relief holder that inhibits restriction by tissue growth.

FIGS. 8A and 8B show two states of the strain relief loop portion of the lead with a sixth embodiment of a strain relief holder that inhibits restriction by tissue growth.

DETAILED DESCRIPTION

Embodiments provide an implantable medical system including an implantable medical lead that may be coupled to a stimulation device where the implantable medical lead has a strain relief loop. According to various embodiments, a strain relief loop holder and/or the strain relief loop of the lead itself inhibits restriction by tissue growth of the function of the strain relief loop. This allows the strain relief loop to assist in maintaining the position of the distal end of the lead at the target site during movements of the body of the patient.

Figure 1:
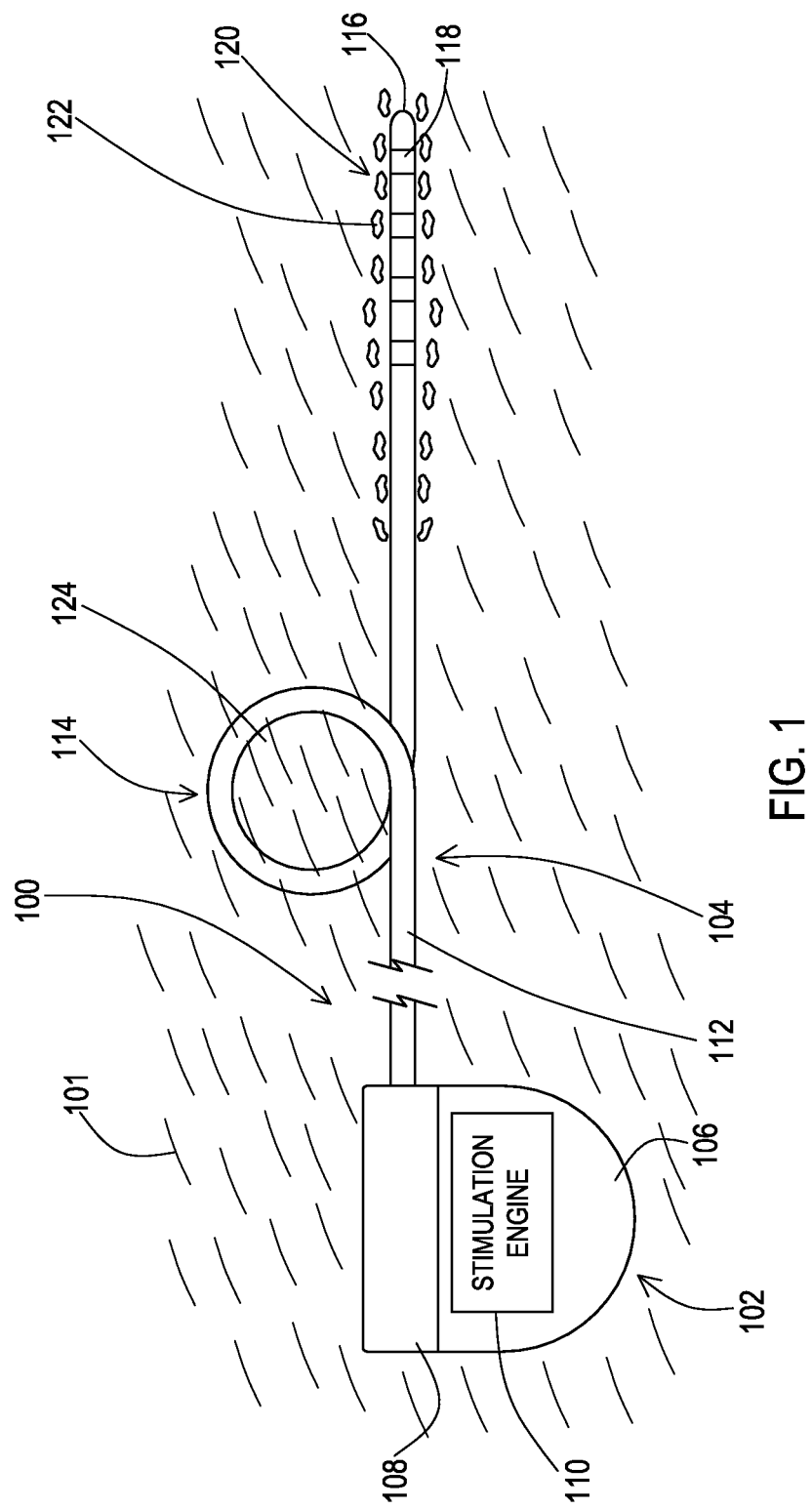
FIG. 1 shows an implantable medical system including a lead having a strain relief loop.

FIG. 1 shows an example of an implantable medical system 100. In this particular view, the implantable medical system 100 is implanted within tissue 101 of a patient. The implantable medical system 100 includes a stimulation device 102 that includes a housing 106 that encloses a stimulation engine 110. A header 108 that is affixed to the housing 106 or is integral to the housing 106 receives a proximal end of an implantable medical lead 104 to establish electrical connectivity to conductors within the lead. The lead 104 provides an electrically conductive pathway from the implantable device 102 to electrodes 118 at a distal end 116 of the lead 104 which is positioned at a target site 120 within the patient. Here, the electrodes 118 are in close proximity to tissue 122 to be stimulated, such as neurological tissue or cardiac tissue.

A lead body 112 of the lead 104 forms a strain relief loop 114 where various embodiments may be present to inhibit restriction of the strain relief loop 114 by tissue growth 124 that otherwise adheres to the strain relief loop 114 within the patient. Here, the electrodes 118 are in close proximity to tissue 122 to be stimulated, such as neurological tissue or cardiac tissue.

A lead body 112 of the lead 104 forms a strain relief loop 114 that is subject to restriction by tissue growth 124. Various embodiments may be present at the strain relief loop 114 to inhibit restriction by the tissue growth 124 that otherwise adheres to the strain relief loop 114. FIGS. 2-8B show examples of these various embodiments which include various objects and/or coating/dopant configurations for obstructing tissue growth as shown in FIGS. 2-4B. These various embodiments also include various objects that create a mechanical advantage to overcome restriction by tissue growth as shown in FIGS. 5A-8B.

Figure 2:
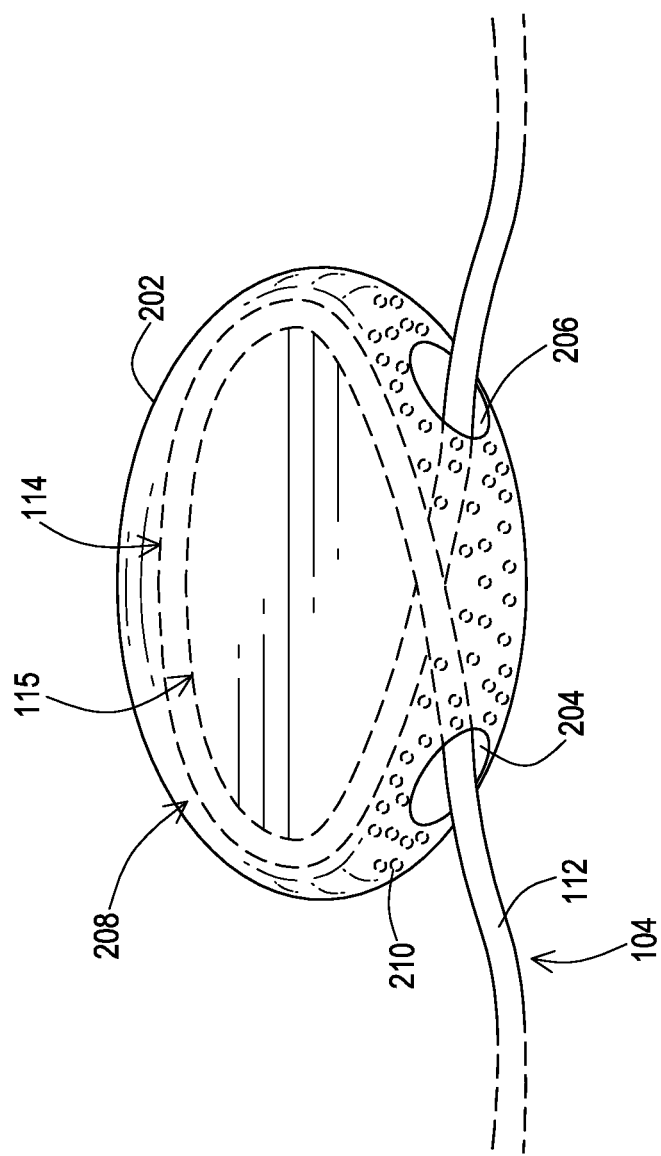
FIG. 2 shows the strain relief loop portion of the lead with a first embodiment of a strain relief holder that inhibits restriction by tissue growth.

FIG. 2 shows an embodiment of an object in the form of a strain relief loop cover 202 that is an enclosure that surrounds the strain relief loop 114. The cover 202 has an entry aperture 204 and an exit aperture 206 that allows the lead body 112 to enter and exit the holder 202 while forming the loop 114 inside of the holder 202. The interior of the cover 202 may be empty space as shown or may have interior details for structural support so long as such details do not restrict the function of the loop 114. The cover 202 obstructs the tissue from being able to grow within the loop 114 as the loop 114 and in particular the surface 115 of the lead body 112 that forms the inner circumference of the loop 114 is effectively isolated from surrounding tissue and tissue growth.

The strain relief loop cover 202 may be constructed of various biocompatible materials, including compliant materials such as polymers including silicones, poly(ethylene), polyurethanes, poly (vinyl chloride), and polylactides and/or rigid materials such as ceramics and metals including stainless steel, cobalt alloys, and titanium alloys. Additionally, the strain relief loop cover 202 may include either a coating or dopant of material 210 that inhibits tissue growth, and in particular inhibits monocyte adhesion and collagen growth. Examples of such a material 210 include synthetic polymers including poly (vinyl alcohol), poly (lactic co-glycolic) acid and poly (lactic acid), oxymatrine, and hydrogels such as poly (hydroxyethyl methacrylate) and polyethylene glycol, and phospholipid-containing materials. This material 210 may be present throughout the cover 202 or at least in areas surrounding the entry aperture 204 and exit aperture 206 so help prevent tissue growth within the apertures 204, 206 that might otherwise restrict the function of the loop 114.

FIG. 3 shows an example of an object in the form of a mesh structure 302 that is present within the loop 114 and is adhered to the surface 115 of the lead body 114 that forms the inner circumference of the loop 114. The mesh structure 302 obstructs the interior of the loop 114 to inhibit tissue from growing through the interior of the loop 114 while being compliant to allow the loop 114 to function. Examples of the material that forms the mesh structure 302 include polymers including silicones, poly(ethylene), polyurethanes, poly (vinyl chloride), and polylactides.

To aid the mesh structure 302 in eliminating tissue growth from the interior of the loop 114, the mesh structure 302 may have a tissue growth inhibitor as a dopant or coating material 304. This material 304 may be the same as the material 210 discussed above in relation to FIG. 2. This material 304 reduces the occurrence of tissue growth onto the mesh structure 302 so that the mesh structure 302 maintains adequate compliance for the loop 114 to function.

FIG. 4A shows an example where there is no object such as a holder or a mesh structure associated with the loop 114. Instead, the lead body 112 has a dopant or coating of material 402 at least in the section forming the loop 114 where the material 402 inhibits tissue growth. While tissue may grow to some degree within the loop 114, the ability of the tissue to grow onto the loop 114 is reduced to thereby preserve at least some of the function of the loop 114. The material 402 may be the same as the material 210 discussed above in relation to FIG. 2.

FIG. 4B shows an example where there is a mesh structure 404 like the mesh structure 302 of FIG. 3, and the lead body 112 also has a dopant or coating of material 402 at least in the section forming the loop 114 where the material 402 inhibits tissue growth as in FIG. 4A. Tissue growth is obstructed within the loop 114 while the ability of the tissue to grow onto the loop 114 is also reduced to further preserve the function of the loop 114.

FIG. 5A shows an example of an object 502 that creates a mechanical advantage to overcome restriction by tissue growth. The object 502 of this example is a pair of arms 504, 508 connected at a hinge point 512 which provides a scissor-like operation. One arm 508 is attached at fixed points 510 along the loop 114 to the lead body 112. The fixation may be provided by a clamping structure on the ends of the arm 508, by an adhesive, by a weld, and the like. The other arm 504 has ends 506 that are loosely coupled to the loop 114 to allow the ends 506 to slide along the loop 114. The arms 504, 508 may be constructed of various rigid and biocompatible materials such as biocompatible plastics or metals.

Figure 5B:
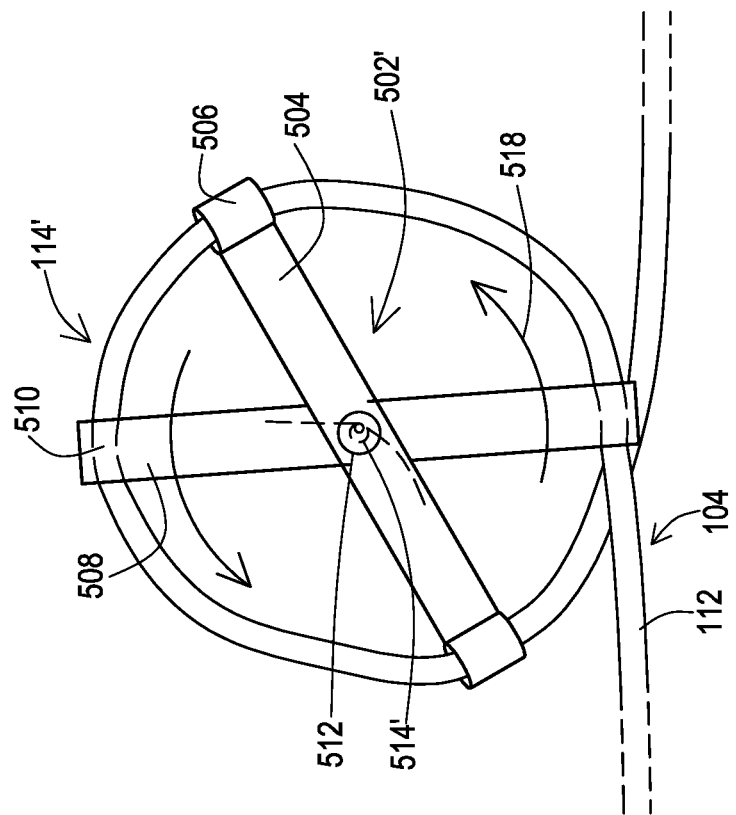

The arms 504, 508 are biased relative to one another to a steady state position shown in FIG. 5A. The bias may be provided by a spring 514 located at the hinge 512 where one side of the spring 514 is attached to the arm 504 and the other side is attached to the arm 508. The arm 504 may be anchored by the presence of tissue and/or by being surgical anchored via suturing or another anchoring technique. The spring 514 causes the arm 508 to resist motion relative to the arm 504, although providing less resistance to motion than the resistance to motion of the distal end 116 of the lead 104. Upon a force 516 being applied due to movement of the patient, the proximal end of the lead moves which overcomes the bias of the spring 514 without dislodging the distal end 116 and causes the arm 508 to rotate away from the steady state position as shown. This rotation in opposition to the bias from the spring 514 results in the state of the object 502' shown in FIG. 5B, where the loop 114' now has a different diameter than the steady state diameter and the spring 514' is stressed relative to the steady state position.

In this example, the force 516 has produced a smaller diameter loop 114' which produces excess lead length that extends toward the proximal end to relieve tension on the distal end 116. When the movement of the patient returns, the excess lead length produced by the reduction in loop diameter should be regained by the loop 114 to increase the loop diameter back to the steady state configuration of FIG. 5A. However, the tissue growth around the loop 114 may constrain the ability of the excess length of the lead body 112 to return to the loop 114, especially considering the loop is compliant and may tend to buckle. The mechanical advantage provided by the bias of the stressed spring 514' effectively pulls the excess length of the lead body 112 back into the loop by the return rotation 518 of the arm 508 as shown in FIG. 5B.

Figure 6B:
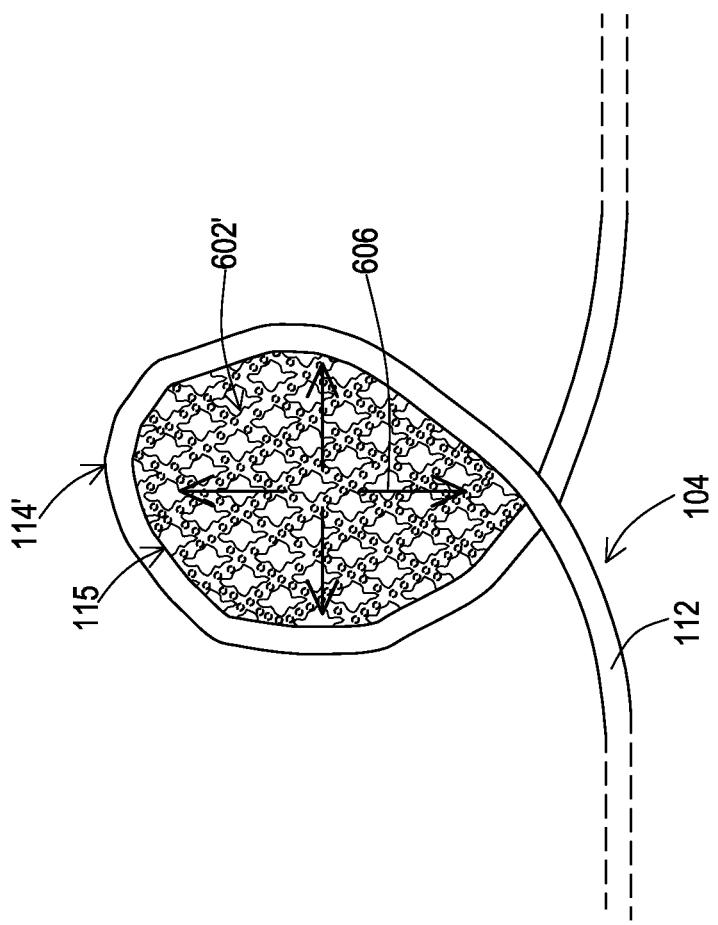

FIG. 6A shows an example of another object 602 that creates a mechanical advantage to overcome restriction by tissue growth. The object 602 of this example is an elastic mesh 602 connected to the surface 115 forming the inner circumference of the loop 114. The elastic mesh 602 has a steady state position shown in FIG. 6A and may resist motion in all directions, although to a lesser degree than the resistance to motion of the distal end 116 of the lead. The elastic mesh 602 may be constructed of various biocompatible materials such as polymers including silicones, poly (ethylene), polyurethanes, poly (vinyl chloride), and polylactides which provide the mechanical advantage by attempting to return to the steady state position. Upon a force 604 being applied due to movement of the patient, the proximal end of the lead moves which causes the mesh 602 to crumple away from the steady state position to the crumpled mesh 602' of FIG. 6B. This movement and resulting crumpling in opposition to the bias from the mesh 602 results in the loop 114' having a different diameter than the steady state diameter.

In this example, the force 604 has produced a smaller diameter loop 114' which produces excess lead length that extends toward the proximal end to relieve tension on the distal end 116. When the movement of the patient returns, the excess lead length produced by the reduction in loop diameter should be regained by the loop 114 to increase the loop diameter back to the steady state configuration of FIG. 6A. However, the tissue growth around the loop 114 may constrain the ability of the excess length of the lead body 112 to return to the loop 114, especially considering the loop is compliant and may tend to buckle. The mechanical advantage provided by the bias 606 of the crumpled mesh 602' forcing the smaller loop 114' to grow in diameter back to the steady state effectively pulls the excess length of the lead body 112 back into the loop 114.

The primary benefit of the mechanical advantage is to assist the strain relief loop in countering the forces exerted by the tissue encapsulation. The goal is to have tissue encapsulation occurring at the strain relief loop last, as per the cover and doping mechanisms discussed above, or in the case of mechanical advantage embodiments, having the effect of the encapsulation (i.e., resisted motion) occurring at the strain relief loop last relative to the effect of the encapsulation at the electrodes.

Figure 7A:
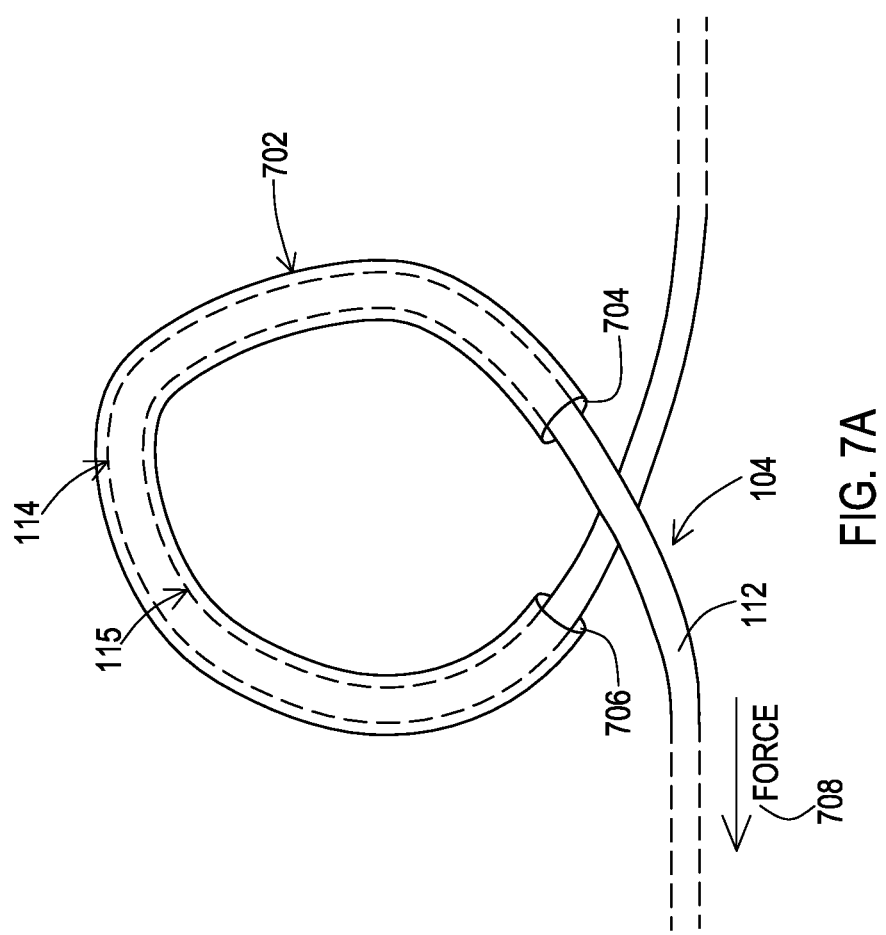
FIGS. 7A and 7B show two states of the strain relief loop portion of the lead with a fifth embodiment of a strain relief holder that inhibits restriction by tissue growth.
Figure 7B:
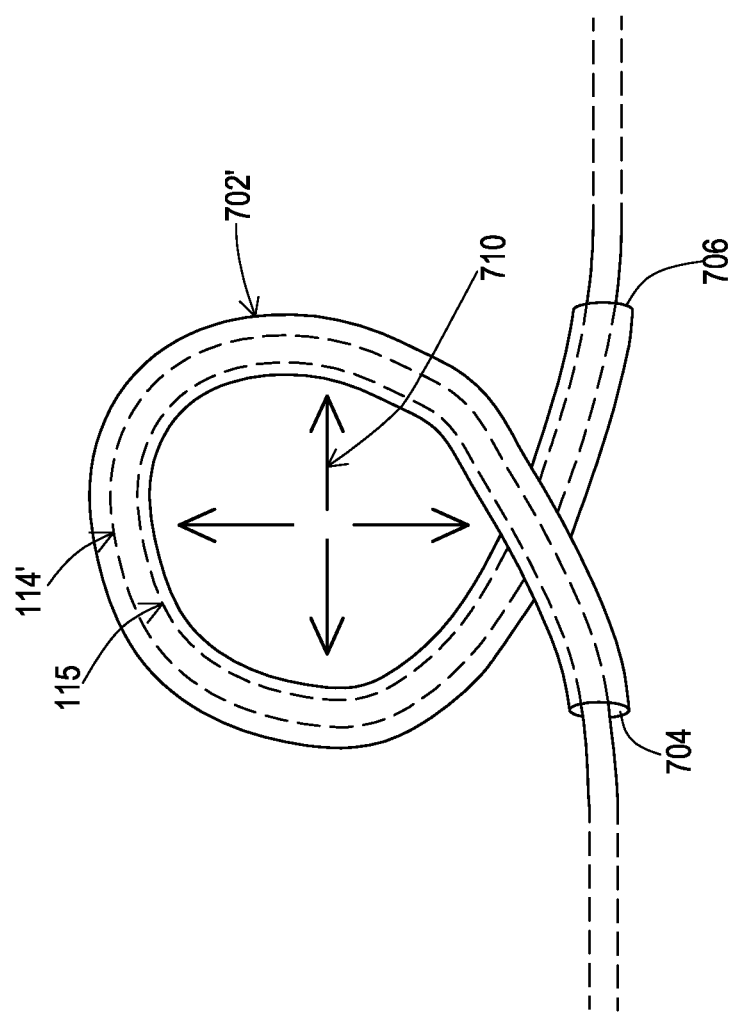

FIG. 7A shows an example of another object 702 that creates a mechanical advantage to overcome restriction by tissue growth. The object 702 of this example is a loop holder in the form of a tubular loop 702 having an entry aperture 704 and an exit aperture 706. The lead body 112 passes through the tubular loop 702 to form the loop 114. The tubular loop 702 has a steady state position shown in FIG. 7A and may resist motion in all directions, although to a lesser degree than the resistance to motion of the distal end 116 of the lead. The tubular loop 702 may be constructed of various materials such as polymers including silicones, poly(ethylene), polyurethanes, poly (vinyl chloride), and polylactides which produce the mechanical advantage by attempting to return to the steady state position. Upon a force 708 being applied due to movement of the patient, the proximal end of the lead 104 moves which causes the tubular loop 702 to bend to a greater degree away from the steady state position to the smaller diameter tubular loop 702' of FIG. 7B. This movement and resulting reduction in loop diameter in opposition to the bias from the tubular loop 702 results in the loop 114' also having a different diameter than the steady state diameter.

In this example, the force 708 has produced a smaller diameter loop 114' which produces excess lead length that extends toward the proximal end to relieve tension on the distal end 116. When the movement of the patient returns, the excess lead length produced by the reduction in loop diameter should be regained by the loop 114 to increase the loop diameter back to the steady state configuration of FIG. 7A. However, the tissue growth around the loop 114 may constrain the ability of the excess length of the lead body 112 to return to the loop 114, especially considering the loop is compliant and may tend to buckle. The mechanical advantage provided by the bias 710 of the tubular loop 702' forcing the smaller loop 114' to grow in diameter back to the steady state effectively pulls the excess length of the lead body 112 back into the loop 114.

FIG. 8A shows an example of another object 802 that creates a mechanical advantage to overcome restriction by tissue growth. The object 802 of this example is a holder in the form of a polymer mold 802. The lead body 112 is press fit into the polymer mold 802, where the mold 802 may either deform to receive the lead body 112 or may have a pre-formed channel 806 to receive the lead body 112. The lead body 112 forms the loop 114 where the loop 114 is then held by the mold 802. The mold 802 has a steady state position shown in FIG. 8A and may resist motion in all directions, although to a lesser degree than the resistance to motion of the distal end 116 of the lead. The mold 802 may be constructed of various materials such silicones, poly (ethylene), polyurethanes, poly (vinyl chloride), and polylactides which produce the mechanical advantage by attempting to return to the steady state position. Upon a force 804 being applied due to movement of the patient, the proximal end of the lead 104 moves which causes the mold 802 to deform away from the steady state position to the smaller diameter mold 802' of FIG. 8B having the ripples 808. This movement and resulting reduction in loop diameter in opposition to the bias from the mold 802 results in the loop 114' also having a different diameter than the steady state diameter.

In this example, the force 804 has produced a smaller diameter loop 114' which produces excess lead length that extends toward the proximal end to relieve tension on the distal end 116. When the movement of the patient returns, the excess lead length produced by the reduction in loop diameter should be regained by the loop 114 to increase the loop diameter back to the steady state configuration of FIG. 8A. However, the tissue growth around the loop 114 may constrain the ability of the excess length of the lead body 112 to return to the loop 114, especially considering the loop is compliant and may tend to buckle. The mechanical advantage provided by the bias 810 of the mold 802' forcing the smaller loop 114' to grow in diameter back to the steady state effectively pulls the excess length of the lead body 112 back into the loop 114.

While embodiments have been particularly shown and described, it will be understood by those skilled in the art that various other changes in the form and details may be made therein without departing from the spirit and scope of the invention.

What is claimed is:

1. A method of inhibiting tissue growth from restricting a strain relief loop of an implantable medical lead, comprising:
providing a lead body of the lead with a tissue growth inhibitor;
positioning the lead body of the implantable medical lead to produce a strain relief loop such that the tissue growth inhibitor is present at the loop; and
coupling an object directly to the strain relief loop of the lead such that the object is present within the strain relief loop and obstructs an area within the loop while allowing the strain relief loop to provide strain relief.

2. The method of claim 1, wherein providing the lead body with a tissue growth inhibitor comprises including a dopant that is the tissue growth inhibitor within the lead body.

3. The method of claim 1, wherein providing the lead body with a tissue growth inhibitor comprises including a coating that is the tissue growth inhibitor on the lead body.

4. The method of claim 1, wherein the tissue growth inhibitor is a collagen growth or monocyte adhesion inhibitor.

5. The method of claim 1, wherein the object comprises a tissue growth inhibitor.

6. The method of claim 1, wherein the object comprises a mesh material.

7. The method of claim 1, comprising providing a bias to the lead body to create a steady state of the strain relief loop, providing strain relief when a force opposes the bias, and wherein providing the bias returns the strain relief loop to the steady state once the force no longer opposes the bias.

8. The method of claim 7, wherein providing the bias comprises providing the object as a hinged arm that applies the bias to the lead body.

9. An implantable medical lead, comprising:
a lead body;
a tissue growth inhibitor on the lead body, wherein the lead body of the implantable medical lead is positioned to produce a strain relief loop such that the tissue growth inhibitor is present at the loop; and
an object present within and coupled directly to the strain relief loop such that the object obstructs an area within the strain relief loop while allowing the strain relief loop to provide strain relief.

10. The implantable medical lead of claim 9, wherein the tissue growth inhibitor comprises a dopant that is within the lead body.

11. The implantable medical lead of claim 9, wherein the tissue growth inhibitor comprises a coating that is on the lead body.

12. The implantable medical lead of claim 9, wherein the tissue growth inhibitor is a collagen growth or monocyte adhesion inhibitor.

13. The implantable medical lead of claim 9, wherein the object comprises a tissue growth inhibitor.

14. The implantable medical lead of claim 9, wherein the object comprises a mesh material.

15. The implantable medical lead of claim 9, further comprising a biasing element coupled to the lead body to create a steady state of the strain relief loop, such that the strain relief loop provides strain relief when a force opposes the biasing element, and the biasing element returns the strain relief loop to the steady state once the force no longer opposes the biasing element.

16. The implantable medical lead of claim 15, wherein the object comprises the biasing element and wherein the biasing element comprises a hinged arm that applies a bias to the lead body.

* * * * *